United States Patent
Slade

(10) Patent No.: US 10,908,164 B2
(45) Date of Patent: Feb. 2, 2021

(54) APPARATUSES, METHODS, COMPUTER PROGRAM PRODUCTS, AND KITS FOR HI-THROUGHPUT GLYCAN ANALYSIS

(71) Applicant: LIFE TECHNOLOGIES CORPORATION, Carlsbad, CA (US)

(72) Inventor: Peter Slade, St Louis, MO (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 741 days.

(21) Appl. No.: 15/460,491

(22) Filed: Mar. 16, 2017

(65) Prior Publication Data

US 2017/0248606 A1 Aug. 31, 2017

Related U.S. Application Data

(63) Continuation of application No. 14/238,183, filed as application No. PCT/US2012/050391 on Aug. 10, 2012, now abandoned.

(60) Provisional application No. 61/523,184, filed on Aug. 12, 2011.

(51) Int. Cl.
  *G01N 33/68* (2006.01)
  *G01N 27/447* (2006.01)
  *C12Q 1/34* (2006.01)

(52) U.S. Cl.
  CPC ........... *G01N 33/6842* (2013.01); *C12Q 1/34* (2013.01); *G01N 27/44726* (2013.01); *G01N 27/44782* (2013.01); *G01N 27/44791* (2013.01); *G01N 33/6803* (2013.01); *G01N 2333/924* (2013.01);

(Continued)

(58) Field of Classification Search
  CPC ............ G01N 27/447; G01N 27/4491; G01N 27/44782; G01N 27/44743; G01N 27/44756; G01N 2400/38; G01N 33/6803; G01N 33/6842; C25C 3/08; C04B 35/5807; C04B 35/64
  See application file for complete search history.

(56) References Cited

U.S. PATENT DOCUMENTS

| | | | |
|---|---|---|---|
| 5,120,413 A | 6/1992 | Chen et al. | |
| 5,205,917 A | 4/1993 | Klock | |
| 5,258,295 A | 11/1993 | Starr et al. | |

(Continued)

FOREIGN PATENT DOCUMENTS

| | | |
|---|---|---|
| CN | 1109597 | 10/1995 |
| WO | WO-2007/044471 A2 | 4/2007 |
| WO | WO-2013/025527 A1 | 2/2013 |

OTHER PUBLICATIONS

W. Laroy, et al., Glycome mapping on DNA sequencing, Nature Protocols, vol. 1, No. 1, pp. 397-405 (2006) (Year: 2006).*

(Continued)

*Primary Examiner* — Maris R Kessel
(74) *Attorney, Agent, or Firm* — Life Technologies Corporation

(57) ABSTRACT

An apparatus for glycan analysis is disclosed. The apparatus includes a plurality of loading wells adapted to receive a plurality of samples; a plurality of capillaries arranged in correspondence with the loading wells, each of the capillaries including a first portion including a stacking gel and a second portion including a resolving gel; and a plurality of eluting wells arranged in correspondence with the capillaries and adapted to receive a portion of the samples having traversed the capillaries.

15 Claims, 13 Drawing Sheets

All in one glycan preparation and analysis.

(52) U.S. Cl.
CPC ..... *G01N 2400/00* (2013.01); *G01N 2400/38* (2013.01)

(56) References Cited

U.S. PATENT DOCUMENTS

| | | | |
|---|---|---|---|
| 5,308,460 | A | 5/1994 | Mazid et al. |
| 5,539,090 | A | 7/1996 | Parekh et al. |
| 5,591,839 | A | 1/1997 | Miller et al. |
| 5,660,702 | A | 8/1997 | Starr |
| 5,672,881 | A | 9/1997 | Striepeke et al. |
| 5,710,628 | A | 1/1998 | Waterhouse et al. |
| 5,716,508 | A | 2/1998 | Starr |
| 5,747,347 | A | 5/1998 | Hawke et al. |
| 5,770,029 | A | 6/1998 | Nelson et al. |
| 5,798,032 | A | 8/1998 | Khan et al. |
| 6,007,691 | A | 12/1999 | Klock, Jr. |
| 6,048,707 | A | 4/2000 | Klock, Jr. |
| 6,074,827 | A | 6/2000 | Nelson et al. |
| 6,156,178 | A | 12/2000 | Mansfield et al. |
| 6,180,779 | B1 | 1/2001 | Parekh et al. |
| 6,803,225 | B2 | 10/2004 | Contreras et al. |
| 7,252,933 | B2 | 8/2007 | Contreras et al. |
| 7,282,130 | B2 | 10/2007 | Flory |
| 7,507,573 | B2 | 3/2009 | Contreras et al. |
| 2004/0067597 | A1 | 4/2004 | Datwani et al. |
| 2005/0074898 | A1 | 4/2005 | Datwani et al. |
| 2005/0155861 | A1 | 7/2005 | Guzman |
| 2009/0258437 | A1 | 10/2009 | Baginski |
| 2009/0288951 | A1* | 11/2009 | Rapp ............... B01D 57/02 204/455 |
| 2010/0151584 | A1 | 6/2010 | Parsons et al. |
| 2010/0190146 | A1 | 7/2010 | Bynum et al. |

OTHER PUBLICATIONS

L. A. Gennaro, et al., On-Line CE-LIF-MS Technology for the Direct Characterization of N-Linked Glycans from Therapeutic Antibodies, Anal. Chem., vol. 80, pp. 3838-3845 (2008) (Year: 2008).*

B. Nagels, et al., Improved sample preparation for CE-LIF analysis of plant N-glycans, Electrophoresis, vol. 32, pp. 3482-3490 (2011). (Year: 2011).*

S. Honda, et al., Ultramicroanalysis of Reducing Carbohydrates by Capillary Electrophoresis with Laser-Induced Fluorescence Detection as 7-Nitro-2,1,3-benzoxadiazole-Tagged N-Methylglycamine Derivatives, Analytical Biochemistry, vol. 286, pp. 99-111 (2000) (Year: 2000).*

"LabChip—ProfilerPro: High Throughput Screening of Neutral Glycans", *Caliper Life Sciences*, 2010, 1-2.

"Rapid Analysis of N-Glycans on the LabChip GXII Microchip-CE Platform", *Caliper Life Sciences*, 2009, 1-4.

Bi, et al., "Guidance to Biochemical Experiments", *Harbin: Northeast Forestry University Press*, Apr. 2011, 1-4 (152-153).

Bynum, M. et al., "An Integrated Microfluidic LC/MS Chip for Rapid On-line Deglycosylation and Characterization of N-glycans from Recombinant IgG Antibodies", *Agilent Technologies/Agilent Laboratories*, 2009, 1-4.

Chen, Y, "Capillary electrophoresis technology and application", *Chemical Industry Press*, Sep. 30, 2000, 23, 33-36, 182.

EP12823779.9, "Extended European Supplementary Search Report", dated Mar. 5, 2015, 7 pgs.

Fulton, S. et al., "Rapid Sample Prep for N-glycan Analysis Using High Throughput Micro Chromatography", *Prozyme Glyko*—www.assaymap.com, Unknown, 1-6.

Jackson, P., "High-Resolution Polyacrylamide Gel Electrophoresis of Fluorophore-Labeled Reducing Saccharides", *Methods in Enzymology*, vol. 230, 1994, 250-265.

Jackson, P., "The Use of Polyacrulamide-Gel Electrophoresis for the High-Resolution Separation of Reducing Saccharides Labelled with the Fluorophore 8-Aminonaphthalene-1,3,6-trisulphoinic acid", *Biochem. J.*, 270, 1990, 705-713.

Jackson, Peter, "Capillary Electrophoresis of Carbohydrates", Specification for Patent Application from Mewburn Ellis LLP, 2011, 1-64.

Kumar, H. et al., "Use of Fluorophore-Assisted Carbohydrate Electrophoresis (FACE) in the Elucideation of N-Linked Oligosaccharide Structures", *Methods in Biotechnology*, vol. 10: *Carbohydrate Biotechnology Protocols*, 221-234.

Laroy, W. et al., "Glycome Mapping on DNA Sequencing Equipment", *Nature Protocols*, vol. 1, No. 1, 2006, 397-405.

Life Technologies Corporation, "3130 DNA Analyzer/Sequencer", 1-6.

Life Technologies Corporation, "Glycobox: New Technology for Glycan Analysis", 1-8.

Starr, C. et al., "Fluorophore-assisted Carbohydrate Electrophoresis in the Separation, Analysis, and sequencing of Carbohydrates", *Journal of Chromatography A*, 720, 1996, 295-321.

Zhao, "Principle and Application of Biochemical Technology", *Textbook for Higher Education Institutions in the 21st Century—Biological Science Series*; Science Press, Beijing, Fourth Edition, Aug. 2008, 1-4 (330).

* cited by examiner

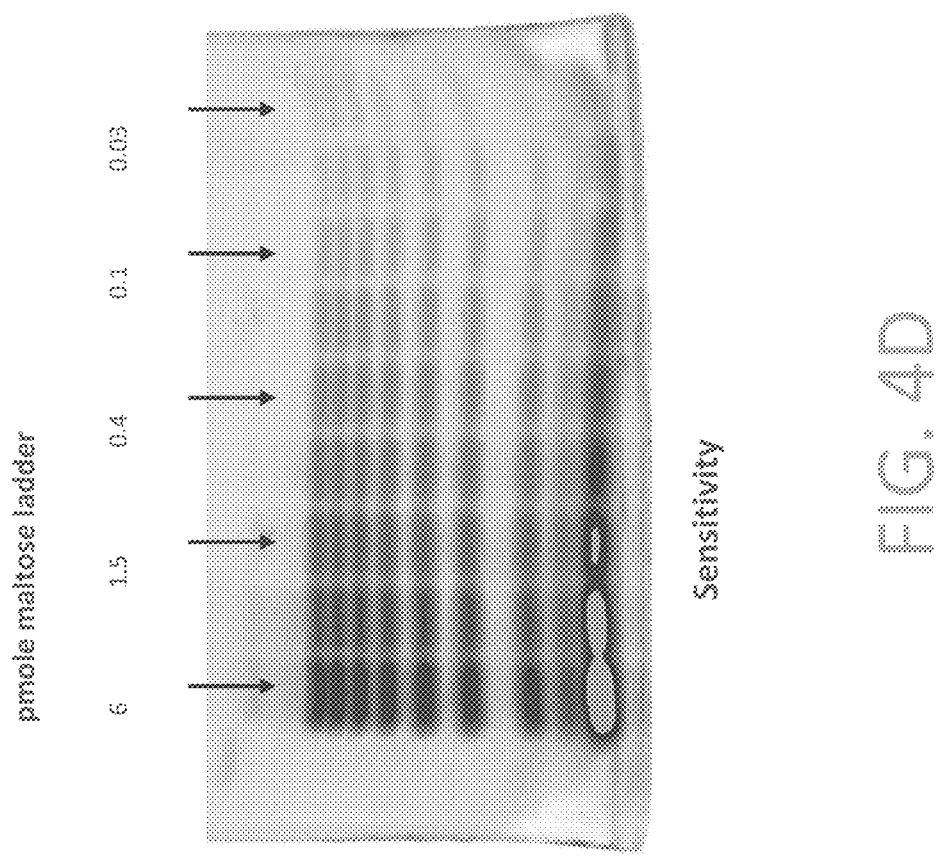

US 10,908,164 B2

APPARATUSES, METHODS, COMPUTER PROGRAM PRODUCTS, AND KITS FOR HI-THROUGHPUT GLYCAN ANALYSIS

CROSS-REFERENCE TO RELATED APPLICATIONS

This application is a Continuation of U.S. application Ser. No. 14/238,183 filed Mar. 25, 2014, which is a 371 of PCT/US2012/050391 filed Aug. 10, 2012, which claims priority to U.S. Application No. 61/523,184 filed Aug. 12, 2011, which disclosures are herein incorporated by reference in their entirety.

BACKGROUND

Field

The present application generally relates to apparatuses, methods, and computer program products for hi-throughput glycan analysis.

Background

Carbohydrates or glycans linked to the surface of proteins play an important role for ensuring correct cellular and protein function and mediating protein folding, signaling, and other important cellular systems. The analysis of glycans is challenging, however, and involves time consuming sample preparation and complex, low-throughput analytical techniques. There is a need for new and improved apparatuses, methods, and computer program products that efficiently and simply allow the performance of hi-throughput analysis of glycans while retaining sufficient resolution and sensitivity. Such a need is especially applicable in numerous fields, including in academic and industrial research and in bioproduction and pharmaceutical industries, for example, where large numbers of glycans need to be analyzed rapidly and efficiently.

SUMMARY

Apparatuses, systems, methods and computer program products for high-throughput glycan analysis are provided.

In one aspect, an apparatus for glycan analysis is provided. The apparatus including: (1) a plurality of loading wells adapted to receive a plurality of samples; (2) a plurality of capillaries arranged in correspondence with the loading wells, each of the capillaries including a first portion including a stacking gel and a second portion including a resolving gel; and (3) a plurality of eluting wells arranged in correspondence with the capillaries and adapted to receive a portion of the samples having traversed the capillaries.

In one aspect, an array of capillaries for glycan analysis is provided. The array of capillaries including: (1) at least five capillaries arranged substantially parallel to one another, each of the capillaries including a pre-poured stacking gel arranged in a first section of the capillary and a pre-poured resolving gel arranged in a second section of the capillary, and (2) first and second support structures arranged at opposite sides of the at least five capillaries such that the at least five capillaries form a single unit.

In one aspect, a library of information elements stored in a medium readable by a computer is provided. The library of information including: (1) a plurality of empirically-derived capillary migration times corresponding to a plurality of individual charged, fluorescently-labeled glycans having migrated through a capillary including a first portion including a stacking gel and a second portion including a resolving gel upon subjection of the capillary to an electric field; and (2) a migration time corresponding to a dextran ladder.

In one aspect, a method for high throughput glycan analysis is provided. The method including: (1) loading a plurality of glycoprotein samples in a plurality of loading wells; (2) denaturing the glycoprotein samples in the loading wells using a denaturing solution; (3) cleaving a glycan from each of the denatured glycoprotein samples in the loading wells using a glycan cleaving enzyme; (4) labeling the cleaved glycans with a charged fluorescent label; and (5) applying an electric field configured to migrate the labeled glycans from the loading wells across an ion permeable membrane and into and along one of a plurality of capillaries arranged in correspondence with the loading wells, each of the capillaries including a first portion including a stacking gel and a second portion including a resolving gel; (6) exciting the labeled glycans migrating along the capillaries with a light source adapted to cause the labeled glycans to emit fluorescent radiation; (7) detecting fluorescent radiation emitted by the labeled glycans; and (8) analyzing the labeled glycans based on the detected fluorescent radiation.

In one aspect, a method of making a capillary array for high throughput glycan analysis is provided. The method including: (1) providing a plurality of capillaries; (2) pre-pouring, into each of the capillaries, a stacking gel in a first portion and a resolving gel in a second portion; and (3) connecting the capillaries structurally on opposite sides such that the capillaries are arranged substantially in parallel to one another and form a single unit.

In one aspect a method for generating a glycan database is provided. The method including: (1) empirically obtaining a plurality of empirically-derived migration times corresponding to a plurality of individual charged, fluorescently-labeled glycans having migrated through a capillary including a first portion including a stacking gel and a second portion including a resolving gel upon subjection of the capillary to an electric field; and (2) arranging the collected plurality of empirically-derived migration times in correspondence with a identification information of each of the plurality of individual charged, fluorescently-labeled glycans having migrated through a capillary into a database configured to be accessible by a computer.

In one aspect, a method for identifying a plurality of glycans is provided. The method including: (1) labeling the glycans with a charged fluorescent label; (2) migrating the labeled glycans along a plurality of capillaries oriented along a substantially parallel direction into an electric field, each of the capillaries including a first portion including a stacking gel and a second portion including a resolving gel; (3) determining a migration time relative to a fluorescently labeled dextran standard ladder for each of the labeled glycans based on detected fluorescent radiation emitted by the labeled glycans; and (4) comparing the relative migration time with a database of empirically-derived migration times corresponding to a plurality of individual charged, fluorescently-labeled glycans having migrated through a capillary including a first portion including a stacking gel and a second portion including a resolving gel upon subjection of the capillary to an electric field.

In one aspect, a kit for glycan analysis is provided. The kit including: (1) an array of capillaries for glycan analysis, including at least five capillaries arranged substantially parallel to one another, each of the capillaries including a pre-poured stacking gel arranged in a first section of the capillary and a pre-poured resolving gel arranged in a second section of the capillary, and first and second support structures arranged at opposite sides of the at least five capillaries such that the at least five capillaries form a single unit; (2) a denaturing solution adapted for denaturing glycoproteins; (3) a glycan cleaving enzyme solution adapted for cleaving glycans; and (4) a fluorescent labeling solution adapted for labeling cleaved glycans.

In one aspect, a kit for glycan analysis is provided. The kit including: (1) a denaturing solution adapted for denaturing glycoproteins; (2) a glycan cleaving enzyme solution adapted for cleaving glycans; and (3) a fluorescent labeling solution adapted for labeling cleaved glycans.

The foregoing general description and the following detailed description are exemplary only and are not limiting in any way of the scope of the invention. Other embodiments or variations upon embodiments specifically discussed herein, including various combinations of features of embodiments discussed herein, may be realized from the following detailed description or may be learned by practice of the invention.

BRIEF DESCRIPTION OF THE DRAWINGS

The accompanying drawings illustrate various exemplary embodiments disclosed herein. The drawings are exemplary only and are not in any way limiting of the scope of the invention.

FIGS. 4A-4D illustrate an exemplary capillary array and related glycan resolution and sensitivity data.

DETAILED DESCRIPTION

Figure 1:
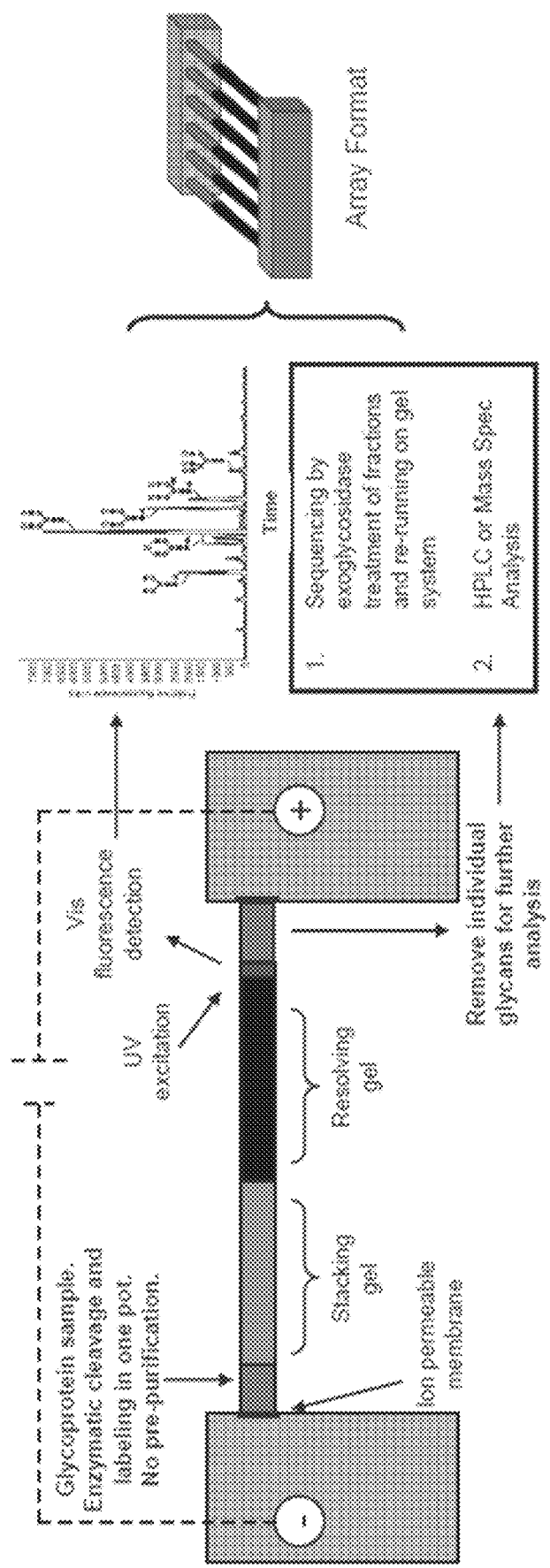
FIG. 1 illustrates an exemplary apparatus for glycan preparation and analysis.

As used herein, the term "antibody" refers to (a) immunoglobulin polypeptides and immunologically active portions of immunoglobulin polypeptides, i.e., polypeptides of the immunoglobulin family, or fragments thereof, that contain an antigen binding site that immunospecifically binds to a specific antigen (e.g., CD70) and an Fc domain comprising a complex N-glycoside-linked sugar chain(s), or (b) conservatively substituted derivatives of such immunoglobulin polypeptides or fragments that immunospecifically bind to the antigen (e.g., CD70). Antibodies are generally described in, for example, Harlow & Lane, Antibodies: A Laboratory Manual (Cold Spring Harbor Laboratory Press, 1988). Unless otherwise apparent from the context, reference to an antibody also includes antibody derivatives as described in more detail below.

As used herein, an "antibody derivative" means an antibody, as defined above (including an antibody fragment), or Fc domain or region of an antibody comprising a complex N-glycoside linked sugar chain, that is modified by covalent attachment of a heterologous molecule such as, e.g., by attachment of a heterologous polypeptide (e.g., a ligand binding domain of heterologous protein), or by glycosylation (other than core fucosylation), deglycosylation (other than non-core fucosylation), acetylation, phosphorylation or other modification not normally associated with the antibody or Fc domain or region.

As used herein, the term "monoclonal antibody" refers to an antibody that is derived from a single cell clone, including any eukaryotic or prokaryotic cell clone, or a phage clone, and not the method by which it is produced. Thus, the term "monoclonal antibody" is not limited to antibodies produced through hybridoma technology.

As used herein, the term "Fc region" refers to the constant region of an antibody, e.g., a $C_{H1}$-hinge-$C_{H2}$-$C_{H3}$ domain, optionally having a $C_{H4}$ domain, or a conservatively substituted derivative of such an Fc region.

As used herein, the term "Fc domain" refers to the constant region domain of an antibody, e.g., a $C_{H1}$, hinge, $C_{H2}$, $C_{H3}$ or $C_{H4}$ domain, or a conservatively substituted derivative of such an Fc domain.

As used herein, the term "low fucosylation" or "reduced fucosylation" does not refer to a single glycoprotein molecule having less fucose residues attached to it. Rather, reference is made to a 'glycoprotein preparation' prepared from cells, or, from a cell medium preparation comprising the glycoproteins secreted by the cell. The glycoprotein preparation comprises a population of individual glycoprotein molecules, with members of the population having different glycosylation features. For purposes of illustration and not limitation, for an IgG1 antibody expressed in a modified CHO cell, "low fucosylation" or "reduced fucosylation" refers to a smaller number of individual glycoproteins having a fucose residue on an N-linked GlcNAc residue of a glycan at position 297 of the Fc. Such "low fucosylation" or "reduced fucosylation" refers to a relatively low (or reduced) number of the glycoproteins of the population having fucose residues on them, as compared to, a population of the same glycoprotein made in a cell line that lacks a modification, or a cell line grown in a medium with, say, a fucose analog that reduces fucosylation. By way of illustration, if a glycoprotein is 1% fucosylated as compared with the same glycoprotein made by a wild-type cell, or in a cell culture medium without, say, a fucosylation inhibitor, only 1% of the molecules of Fc-containing protein are fucosylated as compared with the amount of fucosylation observed in a corresponding wild-type cell (arbitrarily set to 100%, whether or not all of the molecules of Fc-containing protein are fucosylated in the wild-type cell under the same conditions).

Thus, in a "low fucosylation" or "reduced fucosylation" glycoprotein, fucosylation is reduced about 90%, 91%, 92%, 93%, 94%, 95%, 96%, 97%, 98%, or 99% in comparison with a cell that does not contain the modification or a cell not grown in the presence of a fucosylation modifier (for e.g., small molecule like a fucose analog). In a specific embodiment, the reduction is about 99.1%, 99.2%, 99.3%, 99.4%, 99.5%, 99.6%, 99.7%, 99.8%, or 99.9% in comparison with a cell that does not contain the modification, or grown without a fucose inhibitor. In another specific embodiment, the reduction is about 98.1%, 98.2%, 98.3%, 98.4%, 98.5%, 98.6%, 98.7%, 98.8%, or 98.9% in comparison with a cell that does not contain the modification, or grown without a fucose inhibitor. In another specific embodiment, the reduction is about 97.1%, 97.2%, 97.3%, 97.4%, 97.5%, 97.6%, 97.7%, 97.8%, or 97.9% in comparison with a cell that does not contain the modification, or grown without a fucose inhibitor. In another specific embodiment, the reduction is about 96.1%, 96.2%, 96.3%, 96.4%, 96.5%, 96.6%, 96.7%, 96.8%, or 96.9% in comparison with a cell that does not contain the modification, or grown without a fucose inhibitor. In another specific embodiment, the reduction is about 95.1%, 95.2%, 95.3%, 95.4%, 95.5%, 95.6%, 95.7%, 95.8%, or 95.9% in comparison with a cell that does not contain the modification, or grown without a fucose inhibitor. In another specific embodiment, the reduction is about 94.1%, 94.2%, 94.3%, 94.4%, 94.5%, 94.6%, 94.7%, 94.8%, or 94.9% in comparison with a cell that does not contain the modification, or grown without a fucose inhibitor.

Figure 2:
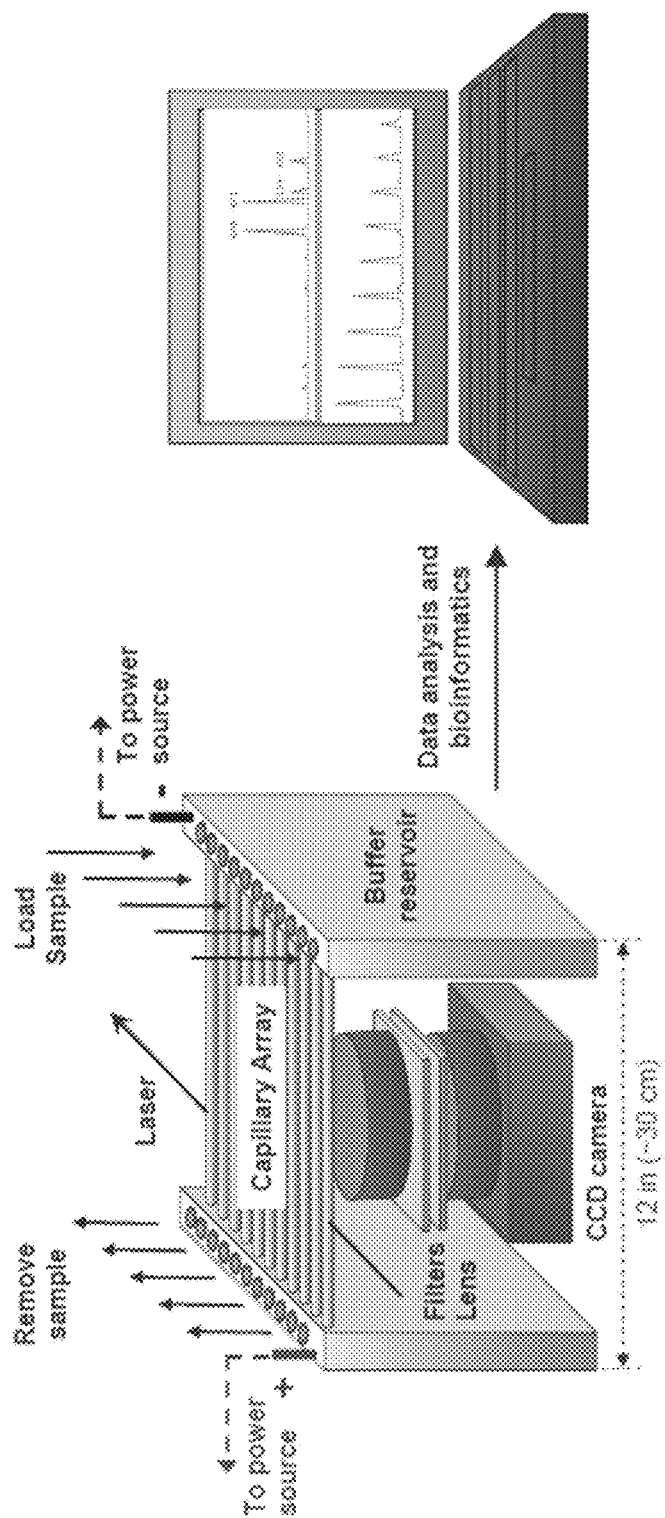
FIG. 2 illustrates an exemplary system for glycan preparation and analysis.

FIG. 1 illustrates an exemplary apparatus for glycan preparation and analysis, which may simplify glycan analysis by performing both sample preparation and analysis with a high-throughput array screening technique and a high resolution analytical technique for complex glycoforms. The apparatus may purify individual glycans and may also be used for protein separation. FIG. 2 illustrates an exemplary system for glycan preparation and analysis, including a capillary array within an apparatus in communication with a computer having a glycan database and identification software.

According to various exemplary embodiments, N-linked glycans may be enzymatically cleaved using PNGase, and glycans may be fluorescently labeled at their reducing end with a modified dye (e.g., ALEXA FLUOR 448, etc.) containing either a hydrazide or oxyamine functional group (e.g., a carbonyl reactive group) on-line, in a 100 microliters sample well. Labeling may involve the formation of a hydrazone between a sugar carbonyl and the fluorophore hydrazide or the formation of an oxime between the sugar carbonyl and the fluorophore hydroxylamine. The labeled glycans may inherit a negative charge due to sulfonic acids that may be in the dye and, as a result, they may migrate in an electric field. The labeled glycans may then be separated by capillary gel electrophoresis and may be detected by fluorescence using, for example, a laser diode (e.g., 488 nm) for excitation and a CCD camera (including, e.g., a 510 nm bandpass filter) for detection, for example. Detection may generate an electrophoretogram showing peaks representing individual glycans as they migrate paste the laser/detector. The ALEXA FLUOR 448 may provide fluorescence at a sufficient linear range to be used quantitatively.

As shown in FIG. 1, the glycans may be separated using a capillary 10 subjected to an electric field (generated by a positive electrode 3 and negative electrode 1 interfaced to opposite ends of the capillary 10) of about 200-400 V/cm with a run time of about 10-15 min. The capillary 10 can include a stacking capillary gel portion 5 comprised of about 4% to 8% acrylamide (or an equivalent gel matrix) and a resolving (analytical) capillary gel portion 6. In various embodiments, the resolving capillary gel portion 6 can be packed into the capillary 10 after the stacking capillary gel portion 5. The resolving capillary portion can be comprised of about 25% to 35% acrylamide (or an equivalent gel matrix). The total capillary 10 length (stacking portion 5 and resolving portion 6) can be between about 5 cm to about 15 cm, and the capillaries may be arranged in an array 12 of up to about twenty capillaries 10. Each capillary 10 may have an internal diameter of about 200 micrometers to ensure sufficient resolution and sensitivity to analyze complex samples. The system may have a detection limit of between about 1 femtomole and 100 attomoles of glycan. For greater sensitivity and resolution, capillaries with a smaller internal diameter of 50-100 micrometers may be used.

According to various embodiments, the above apparatuses, systems and procedures may be used to prepare and purify individual glycans. Specifically, immediately following fluorescent detection, the glycans may be eluted from the end of the capillary array 12 into a sample removal well, where they may be removed (purified) by a technician/researcher for further analysis (e.g., mass spectrometry). This advantageously allows for the development of a retention time database for glycan identification. For higher throughput or purification of greater quantities of glycan a larger capillary array, which may have larger internal diameter of about 1 mm, may advantageously be used.

According to various embodiments, the glycans may be identified by comparison of their retention times (on the electrophoretogram) against a dextran ladder standard (e.g., fluorescently labeled carbohydrate oligomers differing by one glucose molecule). The dextran ladder may be run in parallel with the glycan samples, and specific glycans may then be identified by locating the time point at which they elute relative to the dextran ladder. Known retention times for specific glycan structures and molecular weights may previously be recorded in an empirically-derived database, which may then be searched. An analysis software may then compare retention times (relative to the dextran ladder) of peaks from an electrophoretogram of unknown glycans with the retention time database to identify the glycans. The software may include a database specific for IgG glycans, among other glycans and glycoforms.

According to various embodiments, the above systems and procedures may be used not only for glycan separation and detection, but also for protein separation/purification using SDS-PAGE capillaries. In this case, the capillaries may have an internal diameter of about 1 mm and may contain a 4-12% gradient of acrylamide.

According to various embodiments, the above systems and procedures may be used for easier sample preparation (e.g., on-line labeling) and to complete analysis from glycoprotein to identified glycan much more quickly, potentially in hours instead of days and perhaps even in minutes eventually.

According to various embodiments, the above systems and procedures may be used with multiple ALEXA FLUOR fluorophores (e.g., ALEXA FLUOR 350 hydrazide, ALEXA FLUOR 488 hydrazide, ALEXA FLUOR 647 hydrazide, ALEXA FLUOR 594 hydrazide, and ALEXA FLUOR 555 hydrazide, etc.). The brightness of the ALEXA FLUOR fluorophores may allow for greater sensitivity, and the use of multiple colors of ALEXA FLUOR may allow for the relative quantification of glycans between different samples.

According to various embodiments, the above systems and procedures may be used to simplify sample preparation. The gel matrix may handle relatively "dirty" samples containing protein and salt contaminants, which may reduce sample preparation time, and the hydrazine ALEXA FLUOR may facilitate labeling, on-line and without acid use. Glycan structure being extremely complex, it can be impractical to make synthetic standards.

According to various embodiments, the purification ability of the above systems and procedures may allow the development of a database for glycan identification. Such a database of glycan retention times and glycan identification software advantageously would allow the average biologist/scientist who is unfamiliar with mass spectrometry to be able to do high end glycan analysis.

According to an exemplary embodiment, there is provided an apparatus for glycan analysis, including: (1) a plurality of loading wells 2 adapted to receive a plurality of samples; (2) a plurality of capillaries 10 arranged in correspondence with the loading wells 2, each of the capillaries 2 including a first portion including a stacking gel 5 and a second portion including a resolving gel 6; and (3) a plurality of eluting wells 4 arranged in correspondence with the capillaries 10 and adapted to receive a portion of the samples having traversed the capillaries 10.

In the apparatus, each of the loading wells 2 may be a conduit leading to one of the capillaries 10. Each of the loading wells 2 may be a receptacle in fluid communication through an ion permeable membrane 8 with one of the capillaries 10. Each of the loading wells 2 may have a volume capacity of between about 10 μl and about 500 μl, or of between about 50 μl and about 150 μl, for example. Each of the eluting wells 4 may have a volume capacity of between about 10 μl and about 500 μl, or of between about 50 μl and about 150 μl, for example. The apparatus may further include a reservoir including a buffer solution, the reservoir 15 being in fluid communication through an ion permeable membrane 8 with the loading wells 2. The buffer solution may be TBE. The apparatus may further include a sample loader configured to load samples in the loading wells.

The capillaries 10 may be substantially parallel to one another. The capillaries 10 may have a substantially circular cross-section, or may have a substantially rectangular cross-section, for example. The capillaries 10 may be connected structurally to form a capillary array unit 12 that is removable as a whole. The capillary array unit 12 may be configured for a single use and disposable. Each of the capillaries 10 may be configured for a single use and disposable. The stacking gel portion 5 may be a pre-poured stacking gel, and may include between about 4% and about 8% acrylamide, or about 6% acrylamide, for example. The resolving gel portion 6 may be a pre-poured resolving gel, and may include between about 25% acrylamide and about 35% acrylamide, or about 30% acrylamide, for example. In various embodiments, he stacking gel portion 5 may include about 6% acrylamide while the resolving gel portion 6 may include about 30% acrylamide.

A length of the first portion (i.e., stacking gel portion 5) of each capillary 10 may be between about 5 cm and about 15 cm, and a length of the second portion (i.e., resolving gel portion 6) of each capillary 10 may be between about 5 cm and about 15 cm. A total length of the first and second portions of each capillary 10 may be between about 10 cm and about 30 cm, or may be about 10 cm, for example. The capillaries 10 may include at least five capillaries 10, at least ten capillaries 10, or at least twenty capillaries 10, for example. The plurality of capillaries 10 may include at least five capillaries 10 arranged substantially parallel to one another, each of the capillaries 10 including a pre-poured stacking gel arranged in the first portion of the capillary and a pre-poured resolving gel arranged in the second portion of the capillary, the capillaries 10 further including first and second support structures arranged at opposite sides so as to form a single capillary array unit. The capillaries may have an internal diameter of between about 150 micrometers and about 250 micrometers, or between about 50 micrometers and about 100 micrometers, or between about 0.1 millimeter and about 2.5 millimeters, or between about 0.5 millimeter and about 1.5 millimeters, for example.

The apparatus may further include an ion permeable membrane 8 arranged between the loading wells 2 and the capillaries 10. The apparatus may further include at least two electrodes arranged on opposite sides of the capillaries, and the at least two electrodes may be platinum electrodes and may include a positive electrode 1 arranged between the capillaries 10 and the eluting wells 4 and a negative electrode 3 arranged between the capillaries and the loading wells 2. The apparatus may further include a power source connected to the at least two electrodes and configured to subject at least part of the capillaries to an electric field. The electric field may have an intensity of between about 200 V/cm and about 400 V/cm, or of between about 250 V/cm and about 350 V/cm, for example. The apparatus may further include a light source 19 configured to subject the capillaries to electromagnetic radiation, and the light source may be a diode laser, a blue Argon ion laser, or a yellow Krypton ion laser, for example. The electromagnetic radiation may be radiation having a wavelength in the range of about 400-500 nm or in the range of about 500-600 nm, for example. The apparatus may further include a fluorescence detector 14 configured to detect fluorescence emitted from the capillaries, and the fluorescence detector may be a CCD camera or a CMOS camera. The apparatus may further include a bandpass filter 16 arranged between the capillaries and the CCD camera and configured to allow radiation having a wavelength of about 510 nm to pass. The apparatus may be a bench top apparatus, and may have a largest width, depth, or height that does not exceed about twelve inches.

The apparatus may further include a signal processor configured to process a signal related to fluorescence detected by the fluorescence detector, and the signal processor may be configured to generate an electrophoretogram showing peaks representing individual glycans having migrated through the capillaries 10 so as to reveal a time point at which each glycan passed across the fluorescence detector 16 before eluting off the end of the capillary 10. The apparatus may further include a computer 20 in communication with the fluorescence detector 14, the computer 20 being configured to process a signal related to fluorescence detected by the fluorescence detector 14. The computer 20 may be configured to generate an electrophoretogram showing peaks representing individual glycans having migrated through the capillaries 10 so as to reveal a time point at which each glycan passed across the fluorescence detector 14 before eluting off the end of the capillary 10. The computer 20 may include or be configured to access an empirically-derived database of glycan migration times, and may include or be configured to access and run a computer program product configured to consult the empirically-derived database of glycan migration times to compare migration times obtained by running an experiment with the apparatus to identify individual glycans having migrated through the capillaries 10 during the experiment.

According to an exemplary embodiment, there is provided an array of capillaries 12 for glycan analysis, including: (1) at least five capillaries arranged substantially parallel to one another, each of the capillaries including a pre-poured stacking gel 5 arranged in a first section of the capillary and a pre-poured resolving gel 6 arranged in a second section of the capillary, and (2) first and second support structures arranged at opposite sides of the at least five capillaries such that the at least five capillaries form a single unit.

The capillary array unit 12 may be configured for a single use and disposable. The stacking gel portion 5 may include between about 4% and about 8% acrylamide, or about 6% acrylamide, for example. The resolving gel portion 6 may include between about 25% acrylamide and about 35% acrylamide, or about 30% acrylamide, for example. In various embodiments, the stacking gel portion 5 may include about 6% acrylamide while the resolving gel portion 6 may include about 30% acrylamide, for example.

A length of the first portion of each capillary 10 may be between about 5 cm and about 15 cm, and a length of the second portion of each capillary 10 may be between about 5 cm and about 15 cm. A total length of the first and second portions of each capillary 10 may be between about 10 cm and about 30 cm, or may be about 10 cm, for example. The capillary array 12 may include at least five capillaries, at least ten capillaries, or at least twenty capillaries, for example. The array 12 may include at least ten substantially cylindrical capillaries arranged substantially parallel to one another, each of the capillaries including a pre-poured stacking gel 5 arranged in a first section of the capillary and a pre-poured resolving gel 6 arranged in a second section of the capillary 10, or at least twenty substantially cylindrical capillaries arranged substantially parallel to one another, each of the capillaries including a pre-poured stacking gel 5 arranged in a first section of the capillary and a pre-poured resolving gel 6 arranged in a second section of the capillary 10, for example.

The capillaries may have an internal diameter of between about 100 micrometers and about 300 micrometers, or between about 150 micrometers and about 250 micrometers, or between about 50 micrometers and about 100 micrometers, or between about 0.1 millimeter and about 2.5 millimeters, or between about 0.5 millimeter and about 1.5 millimeters, for example. The array 12 may further include an ion permeable membrane 8 arranged on at least one extremity of each of the capillaries.

According to an exemplary embodiment, there is provided a library of information elements stored in a medium readable by a computer, including: (1) a plurality of empirically-derived capillary migration times corresponding to a plurality of individual charged, fluorescently-labeled glycans having migrated through a capillary including a first portion including a stacking gel and a second portion including a resolving gel upon subjection of the capillary to an electric field; and (2) a migration time corresponding to a dextran ladder.

The dextran ladder may include oligomers having an increasing number of glucose molecules, the increasing number going from one glucose molecule to about twenty glucose molecules, or may include a linear oligomer having a plurality of synthesized maltoses, for example. The dextran ladder may be extracted from digested starch. The empirically-derived migration times corresponding to a plurality of individual glycans may include empirically-derived migration times corresponding to a plurality of polysaccharides, or a plurality of oligosaccharides, or a plurality of proteoglycans, or a plurality of glycoproteins, or a plurality of glycolipids, or a plurality of O-linked glycans, or a plurality of N-linked glycans, for example. The library may further include a plurality of empirically-derived electrophoretogram showing peaks representing individual glycans, and may further include an empirically-derived electrophoretogram showing peaks including at least one peak corresponding to a dextran ladder.

Figure 3:
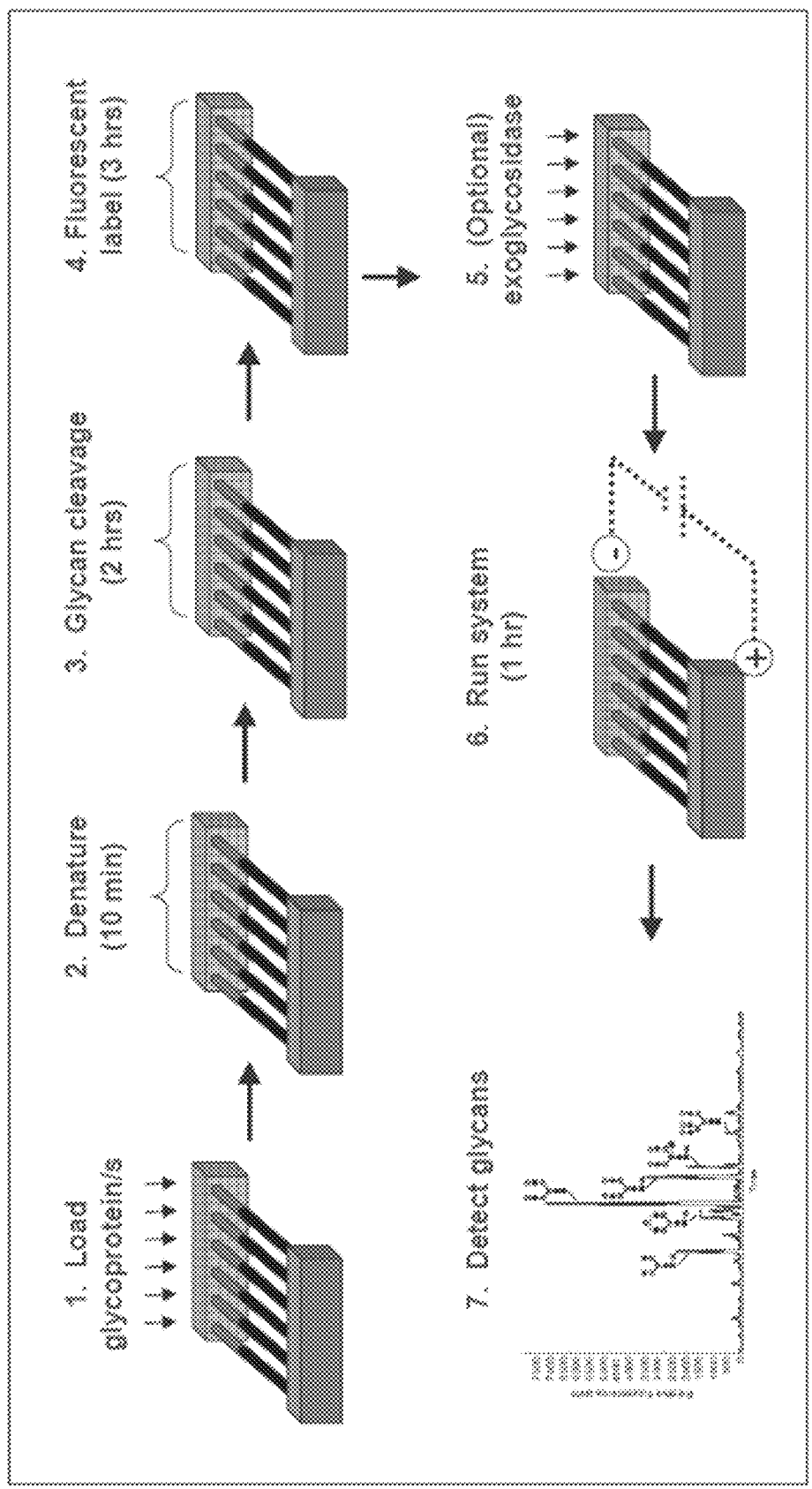
FIG. 3 illustrates an exemplary glycan preparation and analysis workflow.

FIG. 3 illustrates an exemplary glycan preparation and analysis workflow, in accordance with various embodiments. The method can include the following workflow steps: (Step 32) loading a plurality of glycoprotein samples in a plurality of loading wells; (Step 34) denaturing the glycoprotein samples in the loading wells using a denaturing solution; (Step 36) cleaving a glycan from each of the denatured glycoprotein samples in the loading wells using a glycan cleaving enzyme; (Step 38) labeling the cleaved glycans with a charged fluorescent label; (Step 40) applying an electric field configured to migrate the labeled glycans from the loading wells across an ion permeable membrane and into and along one of a plurality of capillaries arranged in correspondence with the loading wells, each of the capillaries including a first portion including a stacking gel and a second portion including a resolving gel and exciting the labeled glycans migrating along the capillaries with a light source adapted to cause the labeled glycans to emit fluorescent radiation; and (Step 42) detecting fluorescent radiation emitted by the labeled glycans; and analyzing the labeled glycans based on the detected fluorescent radiation.

In various embodiments, an optional (Step 44) can inserted into the glycan analysis workflow. (Step 44) involves adding exoglycosidase to the loading wells after the glycans have been labeled in (Step 38).

In various embodiments, loading the glycoprotein samples into the loading wells may include loading each of the glycoprotein samples into a conduit leading to one of the capillaries. In various embodiments, denaturing the glycoprotein samples in the loading wells may include denaturing the glycoprotein samples using SDS. In various embodiments, loading the glycoprotein samples into the loading wells may include loading each of the glycoprotein samples into a receptacle in fluid communication with one of the capillaries, and may include loading between about 10 µl and about 500 µl of each glycoprotein sample into one of the loading wells, or loading between about 50 µl and about 150 µl of each glycoprotein sample into one of the loading wells, for example. In various embodiments, the method may further include mixing each of the glycoprotein samples with a buffer solution, and the buffer solution may be TBE.

In various embodiments, cleaving a glycan from each of the denatured glycoprotein samples may include cleaving the glycans using PNGase F, or using endoglycosidase-H, or using one or more of Endo D, Endo F1, Endo F2, and Endo F3, or using one or more of ABS (arthrobacter ureafaciens sialidase), NAN 1 (recombinant sialidase), AMF (almond meal alpha-fucosidase), BKF (bovine kidney alpha-fucosidase), BTG (bovine testes beta-galactosidase), SPG (*streptococcus peneumoniae* beta-galactosidase), GUH (*streptococcus pheumoniae* hexosaminidase, recombinant in *E. coli*), and JBM (jack bean mannosidase), or using peptide-N—(N-acetyl-β-glucosaminyl)asparagine amidase, for example. Cleaving the glycan using peptide-N—(N-acetyl-β-glucosaminyl)asparagine amidase may include cleaving N-linked glycans.

In various embodiments, labeling the cleaved glycans with a charged fluorescent label may include labeling the cleaved glycans at a reducing end of the glycans with disodium 8-aminonaphtalene-1,3,6-trisulphonate, or with potassium 7-amino-1,3-naphtalene disulfonate, or with sodium 4-amino-naphtalene sulfonate, or with a charged fluorescent label including a hydrazide functional group, or with a charged fluorescent label including one or more of ALEXA FLUOR 350 hydrazide, ALEXA FLUOR 488 hydrazide, ALEXA FLUOR 647 hydrazide, ALEXA FLUOR 594 hydrazide, and ALEXA FLUOR 555 hydrazide, or with a charged fluorescent label including a hydroxylamine functional group contained in one or more of ALEXA FLUOR 350 hydroxylamine, ALEXA FLUOR 488 hydroxylamine, and ALEXA FLUOR 647 hydroxylamine, or with a charged fluorescent label including a hydrazide functional group contained in 8-hydrazide-pyene-3,6,8-trisulfonate, or with a charged fluorescent label including a hydroxylamine functional group contained in 8-hydroxylamine-pyene-3,6,8-trisulfonate, for example. Labeling the cleaved glycans with a charged fluorescent label may include labeling the cleaved glycans at a reducing end of the glycans using one or more of APTS, ANTS, ANDA, and ANSA. The charged fluorescent label may include a sulfonic acid. Labeling may involve the formation of a hydrazone between a sugar carbonyl and the fluorophore hydrazide or the formation of an oxime between the sugar carbonyl and the fluorophore hydroxylamine.

In various embodiments, applying an electric field may include applying an electric field having an intensity of between about 200 V/cm and about 400 V/cm, or between about 250 V/cm and about 350 V/cm, for example, and the electric field may be applied for a period of between about 10 minutes and about 15 minutes, for example. Exciting the labeled glycans may include exciting the labeled glycans with a light source, which may be a laser diode and may have a wavelength in the range of about 400-500 nm or in the range of about 500-600 nm, for example. Detecting fluorescent radiation may include detecting fluorescent radiation using a fluorescence detector, and may includes filtering fluorescent radiation directed to the fluorescence detector using a bandpass filter, which may be a 510 nm bandpass filter.

In various embodiments, analyzing the labeled glycans may include analyzing the labeled glycans based on an electrophoretogram generated by the fluorescence detector or by a signal processor or computer configured to process one or more signals obtained from the fluorescence detector, the electrophoretogram showing peaks representing individual glycans as they migrate along the capillaries and are detected by the fluorescence detector. In various embodiments, analyzing the labeled glycans may include comparing measured migration times to that of a fluorescently labeled dextran standard ladder and to known migration times for specific glycan structures and molecular weights previously recorded in an empirically-derived database.

In various embodiments, loading the glycoprotein samples in the loading wells may further include loading a dextran standard ladder, and analyzing the labeled glycans may be dependent upon their migration time relative to the dextran standard ladder. The dextran ladder standard may include a fluorescently labeled linear polysaccharide made of glucose molecules, including polysaccharide chains having a number of glucose molecules varying by unity increment from one glucose molecule to about twenty-three glucose molecules. The dextran ladder standard may be fluorescently labeled at the reducing end of the sugar chain with the charged fluorescent label including a hydroxylamine functional group contained in the fluorophores ALEXA FLUOR 350 hydroxylamine, or including a hydroxylamine functional group contained in the fluorophores ALEXA FLUOR 647 hydroxylamine, for example. The method may further include eluting labeled glycans from the end of each of the capillaries into a plurality of removal wells arranged in correspondence with the capillaries, and may further include purifying the eluted glycans. The method may further include after having denatured, cleaved, and labeled the glycans, subjecting the glycans to an exoglycosidase enzyme.

According to an exemplary embodiment, there is provided a method of making a capillary array for high throughput glycan analysis, including: (1) providing a plurality of capillaries; (2) pre-pouring, into each of the capillaries, a stacking gel in a first portion and a resolving gel in a second portion; and (3) connecting the capillaries structurally on opposite sides such that the capillaries are arranged substantially in parallel to one another and form a single unit.

In the method, pre-pouring the stacking gel may include pre-pouring a stacking gel including between about 4% and about 8% acrylamide, or about 6% acrylamide, for example. Pre-pouring the resolving gel may include pre-pouring a resolving gel including between about 25% acrylamide and about 35% acrylamide, or about 30% acrylamide, for example. A length of the first portion of each capillary may be between about 5 cm and about 15 cm, and a length of the second portion of each capillary may be between about 5 cm and about 15 cm. A total length of the first and second portions of each capillary may be between about 10 cm and about 30 cm.

Providing a plurality of capillaries may further include providing at least five capillaries, or at least ten capillaries, or at least twenty capillaries, for example. The capillaries may have an internal diameter of between about 100 micrometers and about 300 micrometers, between about 50 micrometers and about 100 micrometers, or between about 0.1 millimeter and about 2.5 millimeters, or between about 0.5 millimeter and about 1.5 millimeters, for example.

According to an exemplary embodiment, there is provided a method for generating a glycan database, including: (1) empirically obtaining a plurality of empirically-derived migration times corresponding to a plurality of individual charged, fluorescently-labeled glycans having migrated through a capillary including a first portion including a stacking gel and a second portion including a resolving gel upon subjection of the capillary to an electric field; and (2) arranging the collected plurality of empirically-derived migration times in correspondence with a identification information of each of the plurality of individual charged, fluorescently-labeled glycans having migrated through a capillary into a database configured to be accessible by a computer.

According to an exemplary embodiment, there is provided a method for identifying a plurality of glycans, including: (1) labeling the glycans with a charged fluorescent label; (2) migrating the labeled glycans along a plurality of capillaries oriented along a substantially parallel direction into an electric field, each of the capillaries including a first portion including a stacking gel and a second portion including a resolving gel; (3) determining a migration time relative to a fluorescently labeled dextran standard ladder for each of the labeled glycans based on detected fluorescent radiation emitted by the labeled glycans; and (4) comparing the relative migration time with a database of empirically-derived migration times corresponding to a plurality of individual charged, fluorescently-labeled glycans having migrated through a capillary including a first portion including a stacking gel and a second portion including a resolving gel upon subjection of the capillary to an electric field.

According to various exemplary embodiments, the apparatus, array or databases for glycan analysis, may further identify the fucosylation status of a recombinant protein or glycoprotein (e.g., whether it is fucosylated or non-fucosylated), or the % fucosylation of a glycoprotein.

Recombinant therapeutic proteins, like antibodies, can undergo a variety of post-translational modifications, including glycosylation, and are commercially produced in large bioreactors in host cells. Antibodies with reduced or low core fucosylation levels (described below) are desirable in the therapeutic industry and have been shown to alter Fc effector functions, in particular, Fc gamma receptor binding and ADCC activity. The glycans attached to Asn297 on antibodies, are usually referred to as having high levels of 'core fucosylation'. Monoclonal antibodies, such as IgG1s, have an N-linked glycosylation site at asparagine 297

(Asn297) of each heavy chain. Alternatively, small molecule inhibitors like catanospermine acting on enzymes in the glycosylation pathway has resulted in antibodies that lack the complex N-linked glycan structure, and therefore has low fucosylation levels. Recently, small molecules, like fucose analogs, have been used in producing recombinant antibodies and derivatives that have complex N-linked glycans but have reduced core fucosylation (see U.S. Publication No. 2009/0317869, whose disclosure is incorporated by reference in its entirety herein). Even more recently, genetically-modified cell lines with reduced ability to fucosylate proteins, but without a knockout of the fucosylating gene, (that is, the modified cell can conditionally fucosylate proteins, say, at a different temperature) have been generated (see U.S. Publication No. 2010/0304436, whose disclosure is incorporated by reference in its entirety herein). These observations have lead to interests in identifying whether antibodies have reduced core fucosylation under certain conditions, and if so, what is the percentage of reduction in glycosylation or fucosylation. The apparatus, arrays and methods of the present invention provide means to identify, characterize and analyze glycoproteins, such as antibodies, for their fucosylation status.

According to various exemplary embodiments, the purification ability of the systems and procedures presented herein and described above, may allow the development of a database for fucosylated or non-fucosylated glycan identification. Such a database of fucosylated versus non-fucosylated glycan retention times and fucosylated versus non-fucosylated glycan identification software advantageously would allow the average biologist/scientist who is unfamiliar with mass spectrometry to be able to do high end glycan analysis. The fucosylated or non-fucosylated glycans may be identified by comparison of their retention times (on the electrophoretogram) with a dextran ladder standard (e.g., fluorescently labeled carbohydrate oligomers differing by one glucose molecule). The dextran ladder may be run in parallel with the glycan samples, and specific glycans may then be identified by locating the time point at which they elute relative to the dextran ladder. Known retention times for specific fucosylated versus non-fucosylated glycan structures and molecular weights may previously be recorded in an empirically-derived database, which may then be searched. An analysis software may then compare retention times (relative to the dextran ladder) of peaks from an electrophoretogram of unknown glycans with the retention time database to identify the specific fucosylated versus non-fucosylated glycans. The software may include a database specific for IgG fucosylated versus non-fucosylated glycans.

According to an exemplary embodiment, there is provided a cell or cell line used in expressing a recombinant glycoprotein in a recombinant cell. In one embodiment, the cell expresses an Fc-containing protein or glycoprotein. In one embodiment, the Fc-containing protein or glycoprotein is an antibody. In certain embodiments, the glycoprotein may be made, either within an unmodified, or a modified cell. Examples of modified cells would be, a cell with a FUT gene knockout, or, a cell that conditionally fucosylates proteins, or, a cell grown in a cell culture medium treated with a sugar analog, like a fucose analog. By fucose analog is meant, a small molecule that inhibits fucosylation, as described below. Exemplary small molecules include, but are not limited to, fucose alkyne, fucose azides, etc., which are described in U.S. Publication No. 2009/0317869, and whose disclosure regarding various small molecule analogs is incorporated by reference in their entirety herein. Thus the cell is cultured in the culture medium under conditions sufficient for the cell to express the protein or glycoprotein. In certain embodiments, the cell itself is the sample that contains the expressed glycoprotein, and in other embodiments, the culture medium that contains the expressed and/or secreted glycoprotein is the sample.

According to an exemplary embodiment, there is provided an array of capillaries for glycan analysis which can identify the fucosylation status of a recombinant protein (whether fucosylated or non-fucosylated), or the % fucosylation of a glycoprotein. Further, in a specific exemplary embodiment of the invention, there is provided a library of information elements stored in a medium readable by a computer which can identify the fucosylation status of a protein, or the % fucosylation of a glycoprotein.

According to another exemplary embodiment, provided herein are methods for high throughput glycan analysis, to identify fucosylated versus non-fucosylated proteins, including: (1) loading a plurality of glycoprotein samples in a plurality of loading wells; (2) denaturing the glycoprotein samples in the loading wells using a denaturing solution; (3) cleaving a glycan from each of the denatured glycoprotein samples in the loading wells using a glycan cleaving enzyme; (4) labeling the cleaved glycans with a charged fluorescent label; and (5) applying an electric field configured to migrate the labeled glycans from the loading wells across an ion permeable membrane and into and along one of a plurality of capillaries arranged in correspondence with the loading wells, each of the capillaries including a first portion including a stacking gel and a second portion including a resolving gel; (6) exciting the labeled glycans migrating along the capillaries with a light source adapted to cause the labeled glycans to emit fluorescent radiation; (7) detecting fluorescent radiation emitted by the labeled glycans; and (8) analyzing the labeled glycans based on the detected fluorescent radiation. In these methods, identification of fucosylation status or % fucosylation may sometimes further include the steps of oligosaccharide analysis via HPLC, wherein fucosyl-containing glycans or oligosaccharides may be quantified by integration of glycan peak area, and, e.g., protein fucosylation may be calculated based on glycan peak area. In some embodiments, the glycoproteins are tagged using click-based sugar analogs that are commercially available from Invitrogen.

In some embodiments, the % fucosylation of one or more glycoproteins may be studied or compared to the % fucosylation of other glycoprotein(s), using the apparatus, the array or various exemplary embodiments of the invention. In one embodiment, the apparatus or the array of capillaries of the invention can identify an expressed glycoprotein of no more than about 5% fucosylated, or in other embodiments, no more than about 4%, 3%, 2%, 1%, 0.5% or 0.1% fucosylated glycoproteins. In a specific embodiment, the percent fucosylation is a mole percent of fucose to glycan. In some embodiments, the cell glycosylates the Fc-containing protein, but does not substantially fucosylate the glycosylated Fc-containing protein. In a specific embodiment, the fucosylation is about no more than about 10%, 5%, 4%, 3%, 2%, 1%, or 0.1% of the fucosylation of the glycosylated Fc-containing protein as compared to a modified cell, or a cell that lacks fucosylation capacities. In yet another specific embodiment, the percent fucosylation is a mole percent of fucose to glycoprotein. In a specific embodiment, the molar ratio of nonfucosylated to fucosylated protein is about 0.90 to 0.10, about 0.91 to 0.09, about 0.92 to 0.08, about 0.93 to 0.07, about 0.94 to 0.06, about 0.95 to 0.05, about 0.96 to 0.04, about 0.97 to 0.03, about 0.98 to 0.02, or about 0.99 to 0.01.

According to an exemplary embodiment, there is provided a kit for glycan analysis, including: (1) an array of capillaries for glycan analysis, including at least five capillaries arranged substantially parallel to one another, each of the capillaries including a pre-poured stacking gel arranged in a first section of the capillary and a pre-poured resolving gel arranged in a second section of the capillary, and first and second support structures arranged at opposite sides of the at least five capillaries such that the at least five capillaries form a single unit; (2) a denaturing solution adapted for denaturing glycoproteins; (3) a glycan cleaving enzyme solution adapted for cleaving glycans; and (4) a fluorescent labeling solution adapted for labeling cleaved glycans.

According to an exemplary embodiment, there is provided a kit for glycan analysis, including: (1) a denaturing solution adapted for denaturing glycoproteins; (2) a glycan cleaving enzyme solution adapted for cleaving glycans; and (3) a fluorescent labeling solution adapted for labeling cleaved glycans.

The denaturing solution may include SDS. The glycan cleaving enzyme solution may include one or more of PNGase F and endoglycosidase-H, or one or more of Endo D, Endo F1, Endo F2, Endo F3, ABS (arthrobacter ureafaciens sialidase), NAN 1 (recombinant sialidase), AMF (almond meal alpha-fucosidase), BKF (bovine kidney alpha-fucosidase), BTG (bovine testes beta-galactosidase), SPG (*streptococcus peneumoniae* beta-galactosidase), GUH (*streptococcus pheumoniae* hexosaminidase, recombinant in *E. coli*), and JBM (jack bean mannosidase), for example.

The fluorescent labeling solution may include one or more of disodium 8-aminonaphtal ene-1,3,6-trisulphonate, potassium 7-amino-1,3-naphtalene di sulfonate, sodium 4-amino-naphtalene sulfonate, a charged fluorescent label including a hydrazide functional group, ALEXA FLUOR 350 hydrazide, ALEXA FLUOR 488 hydrazide, ALEXA FLUOR 647 hydrazide, ALEXA FLUOR 594 hydrazide, ALEXA FLUOR 555 hydrazide, ALEXA FLUOR 350 hydroxylamine, ALEXA FLUOR 488 hydroxylamine, ALEXA FLUOR 647 hydroxylamine, 8-hydrazide-pyene-3,6,8-trisulfonate, 8-hydroxylamine-pyene-3,6,8-trisulfonate, APTS, ANTS, ANDA, and ANSA, for example.

According to various exemplary embodiments described herein, one or more aspects of one or more of the foregoing exemplary embodiments may be performed in whole or in part using a DNA sequencer such as the APPLIED BIOSYSTEMS 3130 Genetic Analyzer, for example.

Figure 4A:
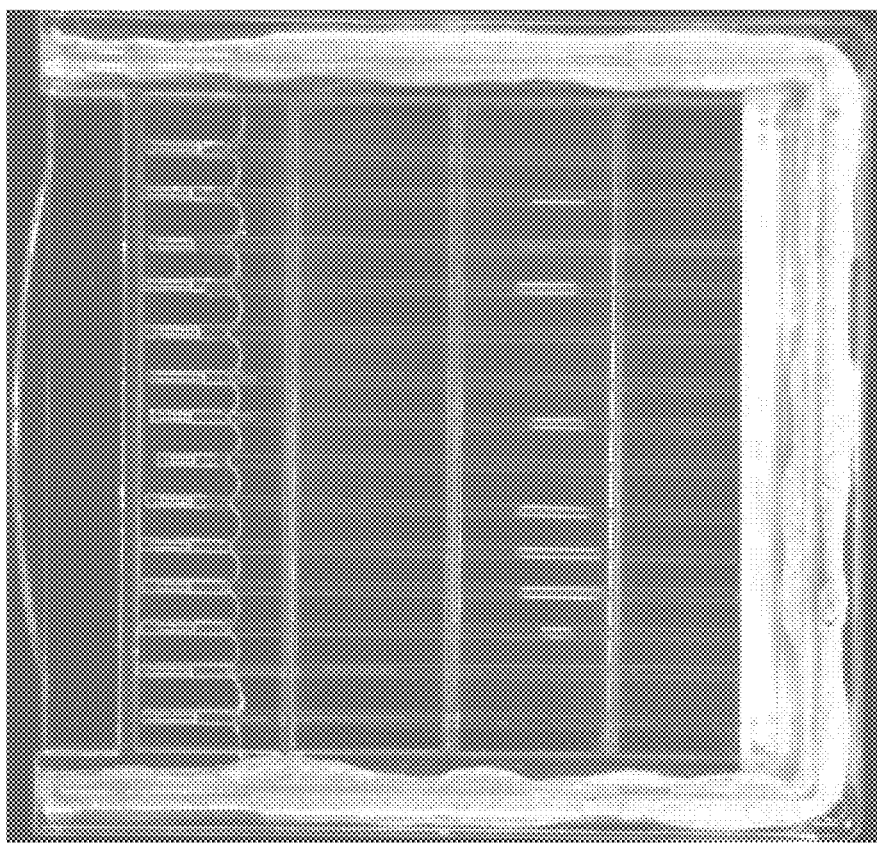
Figure 4B:
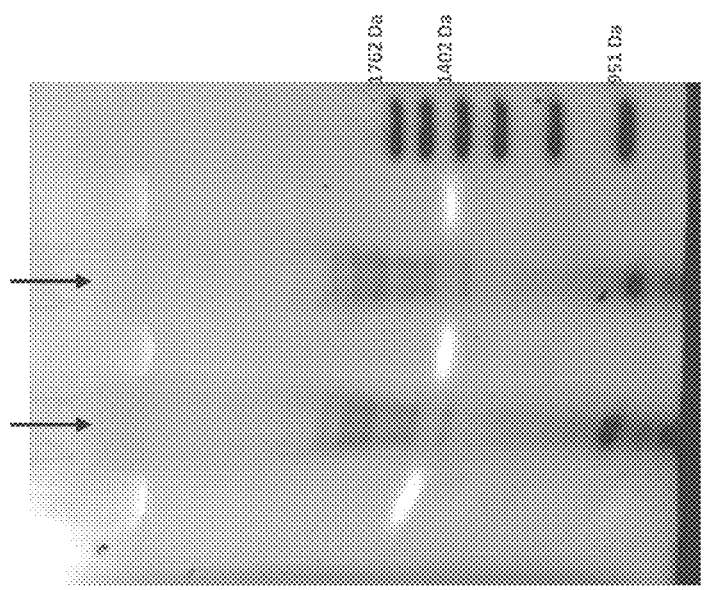
Figure 4C:
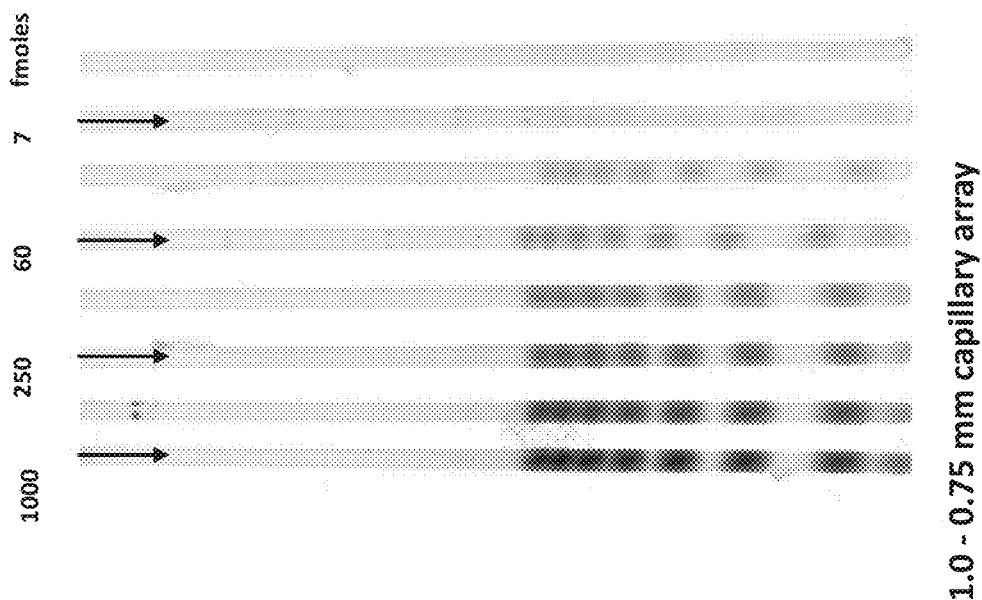
Figure 5:
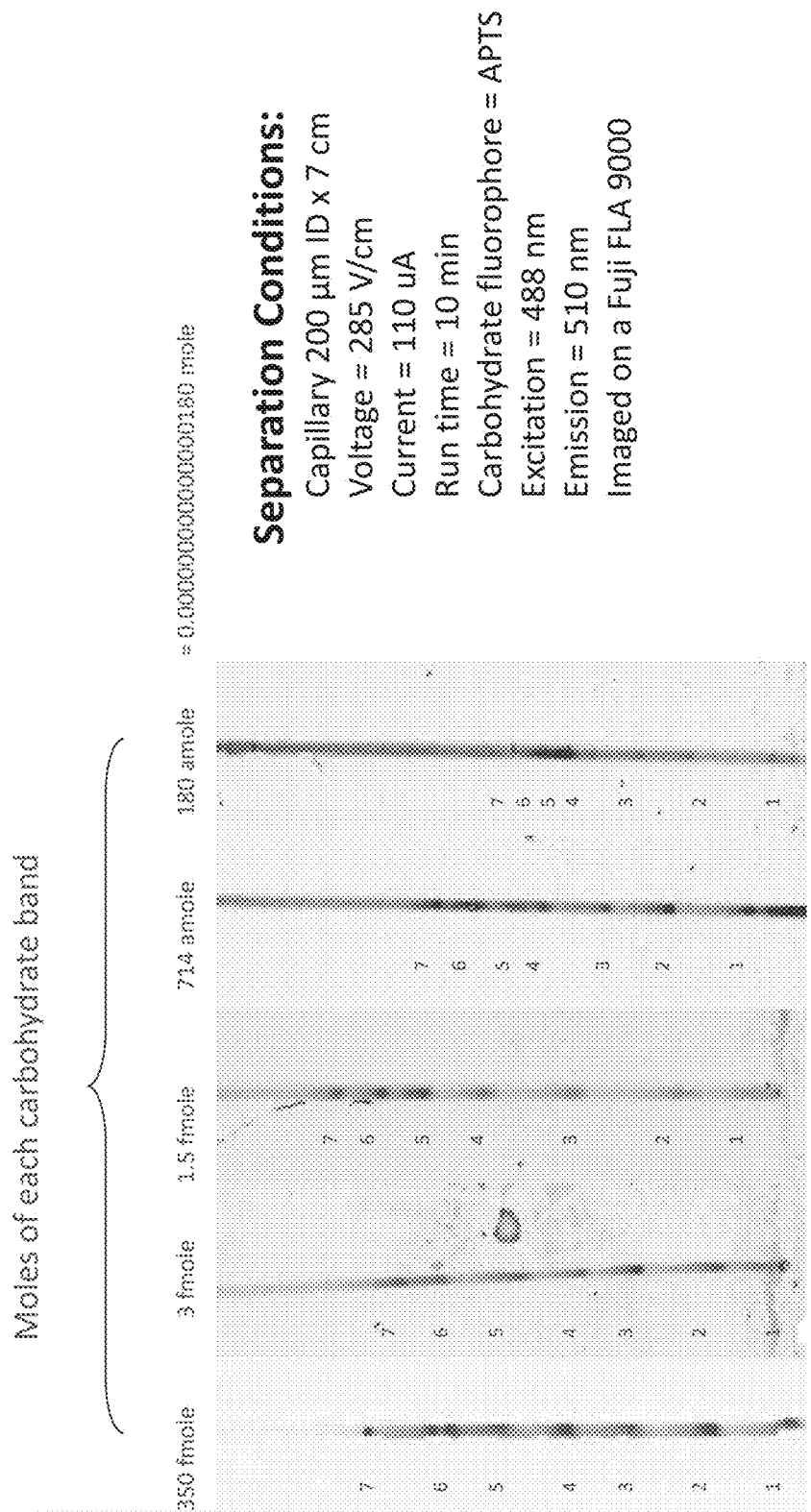
FIG. 5 illustrates capillary gel electrophoresis and glycan resolution and sensitivity data for seven carbohydrates.
Figure 6:
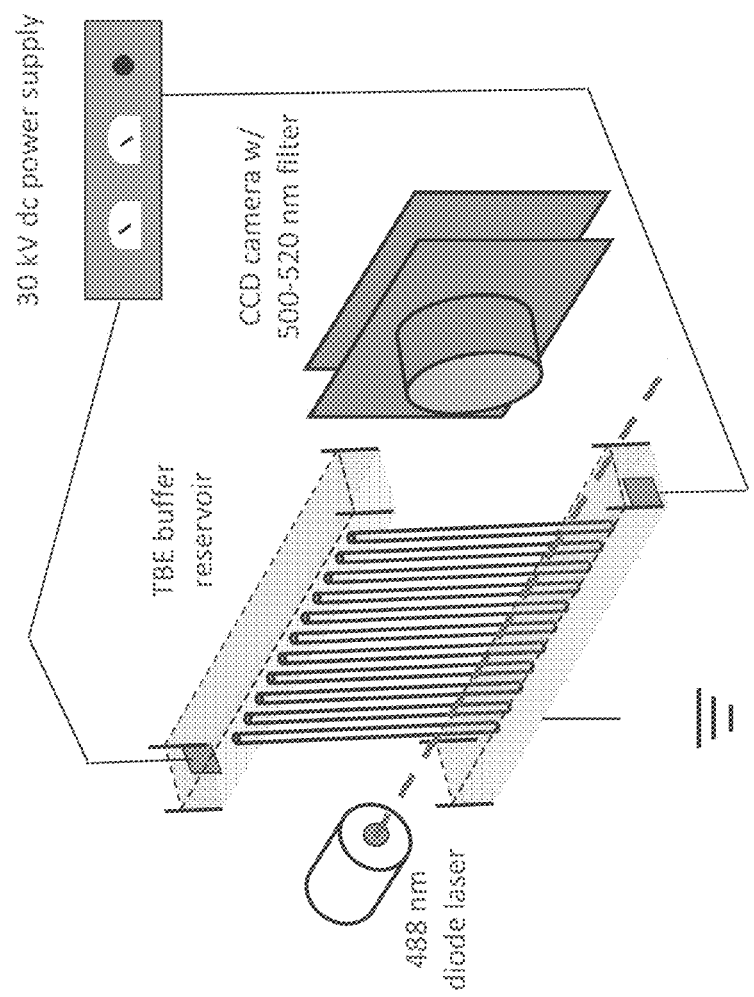
FIG. 6 illustrates an exemplary apparatus for glycan preparation and analysis.
Figure 7:
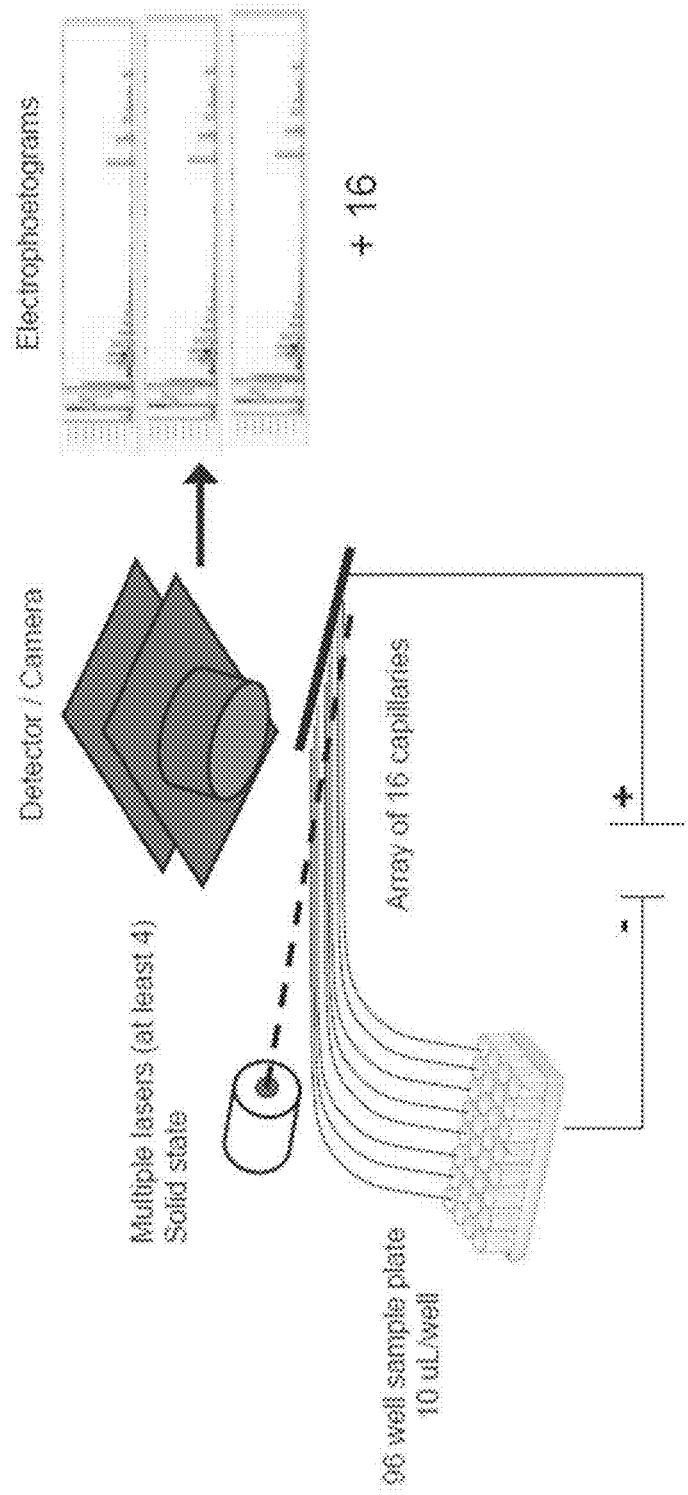
FIG. 7 illustrates an exemplary system and related glycan analysis data.
Figure 8:
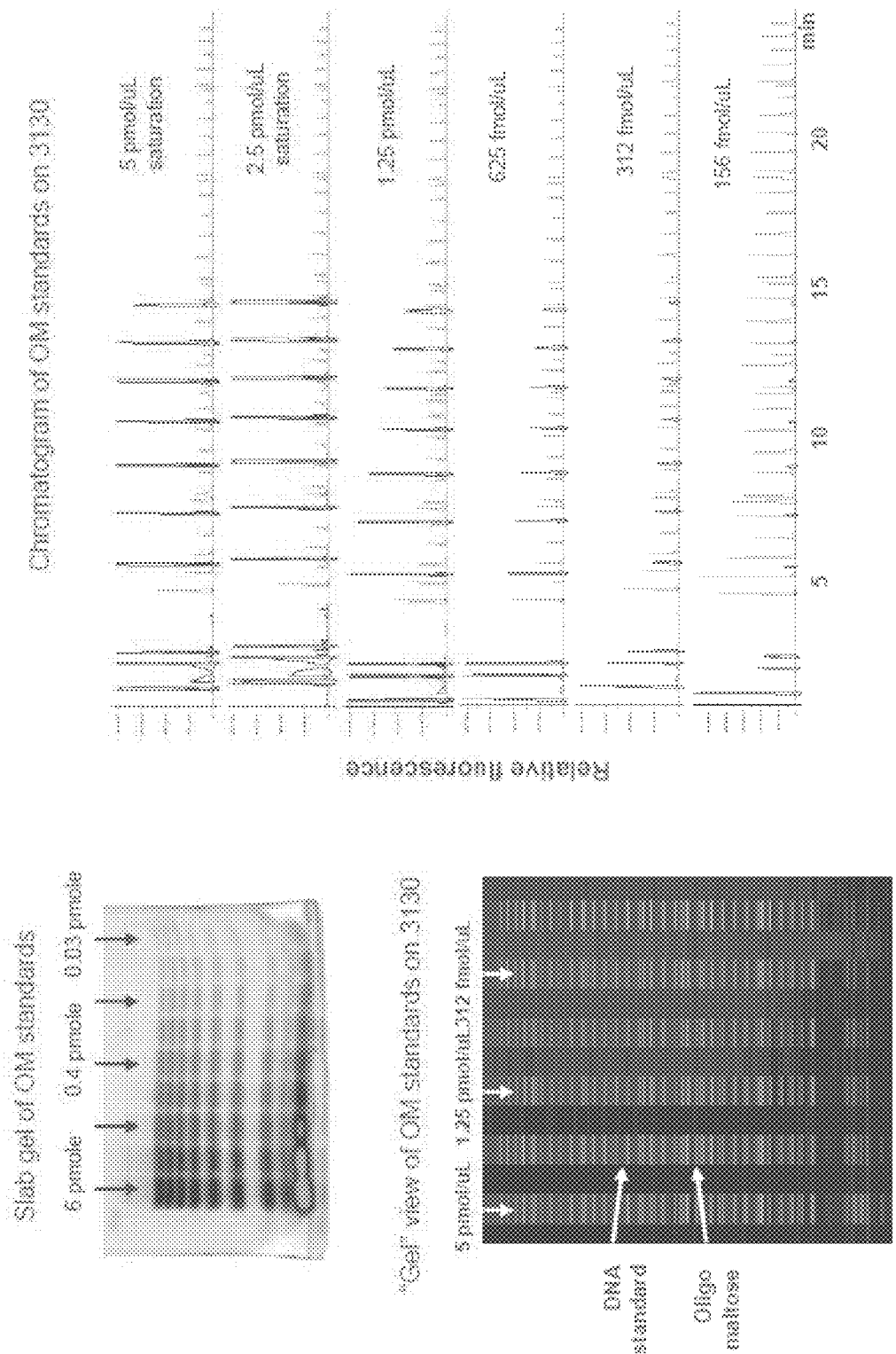
FIGS. 8-10 illustrate various data and electrophoretograms regarding the separation of oligo maltose standards and glycans from IgG and other glycoproteins on a capillary array system; Applied Biosystems® 3130 Genetic Analyzer.
Figure 9:
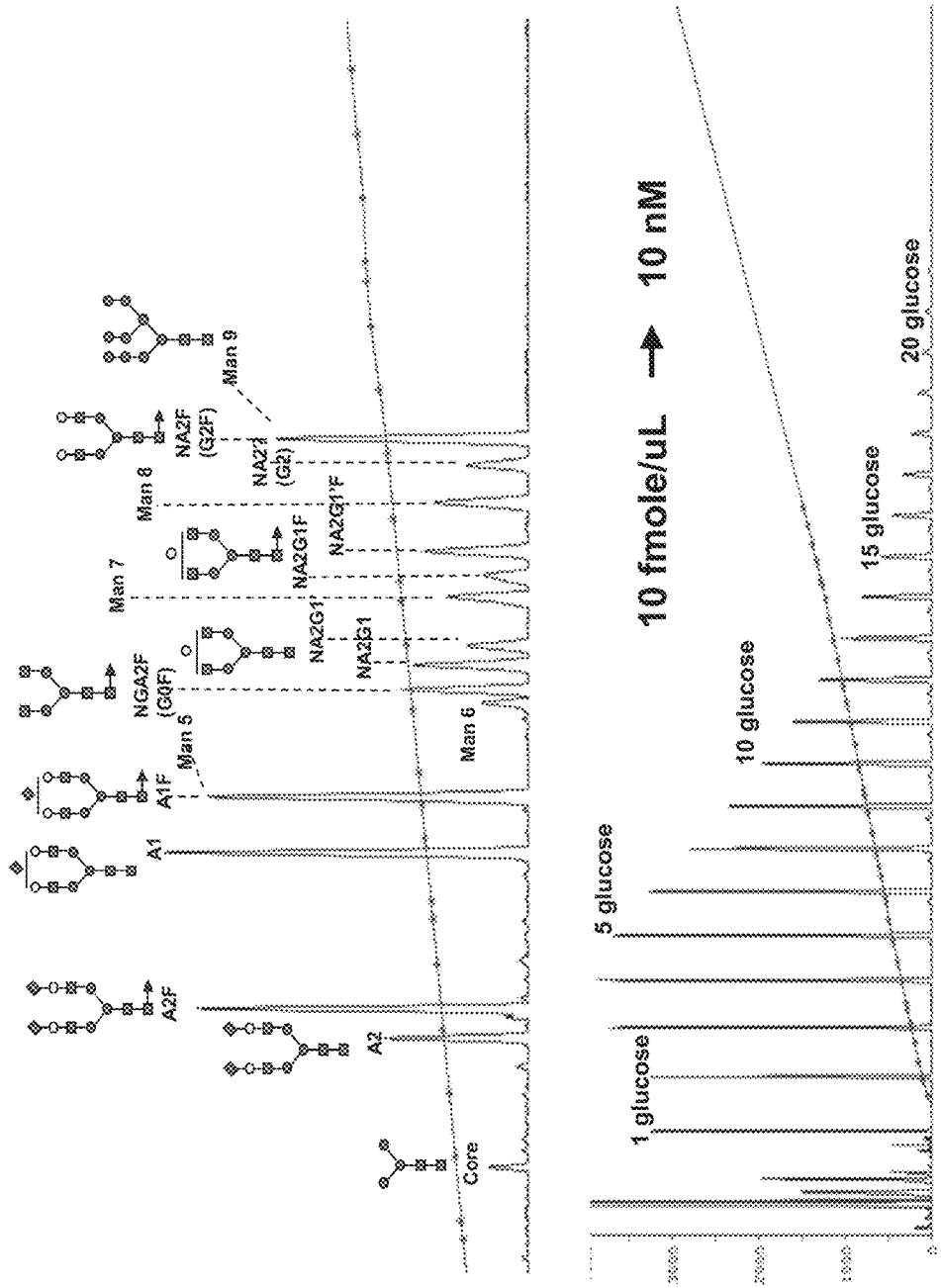
Figure 10:
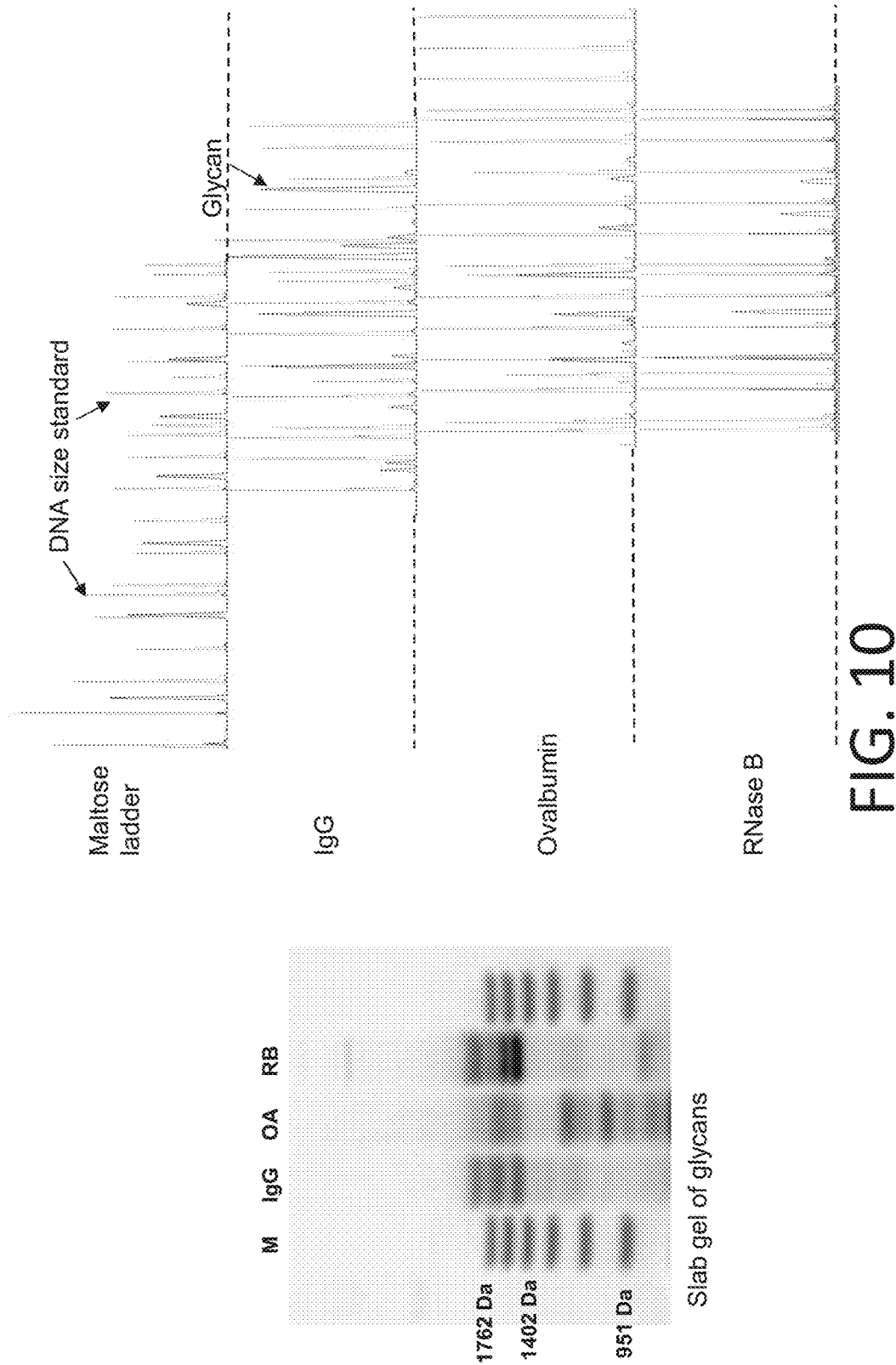

FIG. 4A illustrates an exemplary capillary array. FIGS. 4B-4D illustrate related glycan resolution and sensitivity data. FIG. 5 illustrates capillary gel electrophoresis and glycan resolution and sensitivity data for seven carbohydrates. FIG. 6 illustrates an exemplary apparatus for glycan preparation and analysis. FIG. 7 illustrates an exemplary system and related glycan analysis data. FIGS. 8-10 illustrate various data and electrophorograms regarding the separation of oligo maltose standards and glycans from IgG and other glycoproteins on a capillary array system; Applied Biosystems® 3130 Genetic Analyzer.

Other embodiments of the invention will be apparent to one of ordinary skill in the art having had the benefit of the present specification and/or having practiced one or more embodiments of the invention. Further, the present specification including the drawings are all exemplary and are not in any way limiting of the scope of the invention, which shall be determined by the following claims.

What is claimed is:

1. A method for high throughput glycan analysis, the method comprising:
loading a plurality of samples into a plurality of loading wells, wherein the plurality of samples include glycoproteins;
denaturing the glycoproteins in the loading wells using a denaturing solution;
cleaving one or more glycans from the denatured glycoproteins in the loading wells using a glycan cleaving enzyme;
labeling the cleaved glycans with one or more fluorescent labels to form labeled glycans;
migrating the labeled glycans across a plurality of capillaries by applying an electric field configured to migrate the labeled glycans from the loading wells across an ion permeable membrane and into and along one of a plurality of capillaries arranged in correspondence with the loading wells, each of the capillaries including a first portion including a stacking gel, including between 4% to 8% acrylamide, and a second portion including a resolving gel, including between 25% and 35% acrylamide;
exciting the one or more fluorescent labels of the labeled glycans to generate fluorescence;
detecting the fluorescence emitted by the labeled glycans; and
analyzing the labeled glycans based on the detected fluorescence.

2. The method of claim 1, additionally comprising:
eluting one or more of the labeled glycans from the plurality of capillaries for further analysis.

3. The method of claim 2, wherein the further analysis comprises mass spectrometry or high performance liquid chromatography.

4. The method of claim 2, wherein individual glycans are purified from the one or more of the labeled glycans eluted from the plurality of capillaries.

5. The method of claim 1, wherein denaturing the glycoproteins comprises addition of a denaturing solution into the plurality of loading wells.

6. The method of claim 1, wherein cleaving the one or more glycans from the denatured glycoproteins comprises enzymatic cleavage.

7. The method of claim 6, wherein the enzymatic cleavage involves a plurality of different enzymes.

8. The method of claim 1, wherein the one or more fluorescent labels include a charged fluorescent label.

9. The method of claim 1, wherein the cleaved glycans are labeled at a reducing end.

10. The method of claim 1, wherein exciting the one or more fluorescent labels comprises excitation with a light source.

11. The method of claim 10, wherein the light source is a laser.

12. The method of claim 11, wherein the laser emits electromagnetic radiation having a wavelength in the range of about 400-500 nm or about 500-600 nm.

13. The method of claim 1, wherein detecting the fluorescence includes filtering the fluorescence emitted by the one or more fluorescent labels.

14. The method of claim 1, wherein analyzing the labeled glycans comprises generating an electrophoretogram.

15. The method of claim 13, additionally comprising loading a dextran ladder standard into the plurality of wells, and wherein the electrophoretogram is additionally based upon the dextran ladder standard.

\* \* \* \* \*